(12) United States Patent
Kazazoglu et al.

(10) Patent No.: US 8,545,438 B2
(45) Date of Patent: Oct. 1, 2013

(54) BREAST PUMP

(75) Inventors: H. Sinan Kazazoglu, Izmir (TR); Koji Matsutori, Arlington, VA (US)

(73) Assignee: Lansinoh Laboratories, Inc., Alexandria, VA (US)

( * ) Notice: Subject to any disclaimer, the term of this patent is extended or adjusted under 35 U.S.C. 154(b) by 492 days.

(21) Appl. No.: 12/802,855

(22) Filed: Jun. 15, 2010

(65) Prior Publication Data

US 2010/0324478 A1 Dec. 23, 2010

Related U.S. Application Data

(60) Provisional application No. 61/269,282, filed on Jun. 22, 2009.

(51) Int. Cl.
*A61M 1/06* (2006.01)

(52) U.S. Cl.
USPC .......................................................... 604/74

(58) Field of Classification Search
USPC ........................................................... 604/74
See application file for complete search history.

(56) References Cited

U.S. PATENT DOCUMENTS

| | | | |
|---|---|---|---|
| 6,547,756 B1 | 4/2003 | Greter et al. | 604/74 |
| 7,070,400 B2 | 7/2006 | Greter | 417/413.1 |
| 2004/0024351 A1* | 2/2004 | Greter et al. | 604/74 |
| 2004/0024352 A1* | 2/2004 | Renz et al. | 604/74 |
| 2007/0292276 A1 | 12/2007 | Stutz et al. | 417/137 |

* cited by examiner

*Primary Examiner* — Jason Flick
(74) *Attorney, Agent, or Firm* — Michael W. Ferrell

(57) ABSTRACT

An electronically controlled breast pump for generating cyclical suction includes a cumulative vacuum pump and a plurality of switches including at least an expression mode cycle time selection switch, a peak vacuum level selection switch, and a stimulation mode switch. A controller coupled to the cumulative vacuum pump controls the apparatus which optionally further includes a four-layer assembly of the various features, an adjustable safety valve, and/or a pump head with a groove traversing top dead center of the pump head.

19 Claims, 14 Drawing Sheets

BREAST PUMP

CLAIM FOR PRIORITY

This non-provisional application claims the benefit of the filing date of U.S. Provisional Patent Application Ser. No. 61/269,282, of the same title, filed Jun. 22, 2009. The priority of U.S. Provisional Patent Application Ser. No. 61/269,282 is hereby claimed and the disclosure thereof is incorporated into this application by reference.

TECHNICAL FIELD

The present invention relates to a breast pump including a vacuum pump and a control system therefore. The system provides a plurality of discrete vacuum level settings and a plurality of discrete cycle time settings and is readily switchable between an expression mode and a stimulation mode. A compact 4-layer construction provides better efficiency and ease of manufacture.

BACKGROUND OF THE INVENTION

Electric breast pumps are known in the art. There is disclosed in U.S. Pat. No. 7,070,400 to Greter a diaphragm suction pump without pump chamber dead space. In particular, the '400 patent is directed to a diaphragm pump wherein the pump diaphragm is driven by an electric motor crank mechanism by means of a connecting rod and spans a pump chamber provided in a base plate. The pump chamber walls are provided with a conically widening profile and the various parts are configured such that the diaphragm bears substantially tightly against the entire pump chamber wall along the sides and at a top dead center position of the connecting rod will result in a position where there is substantially no dead space. It has been found that this particular arrangement is undesirable since there is no means to break the vacuum between the diaphragm and the cylinder pump head upon reciprocation of the diaphragm, resulting in "vacuum lock".

U.S. Pat. No. 6,547,756 to Greter et al. discloses a breast pump which can be programmed to generate a plurality of different milk expression sequences. In one embodiment of the invention, a motorized pump is provided with a microprocessor controller.

Also disclosed in pending applications are various features for breast pumps. In this regard, there is disclosed in United States Patent Application Publication No. 2004/0024351 (U.S. patent application Ser. No. 10/413,463) to Greter et al. a breast pump that generates a let-down or stimulation phase and a milk expression phase. See, also, United States Patent Application Publication No. 2007/0292276 (U.S. patent application Ser. No. 11/662,683) to Stutz et al. entitled "Membrane Pump With Bleed Valve." The Stutz et al. application discloses a vacuum pump with a bleed valve which opens partially at an initial stage and later opens to a greater extent during a pump cycle.

While various features and control schemes have been disclosed in the art, electric breast pumps are typically expensive and relatively difficult to operate. There is provided in accordance with the present invention an easy to use, economical breast pump system which provides superior levels of comfort and adjustability without complex operating modes.

SUMMARY OF INVENTION

There is provided in accordance with the invention an electronically controlled breast pump for generating cyclical suction comprising (a) a cumulative vacuum pump with a release valve; (b) a plurality of switches including at least an expression mode cycle time selection switch, a peak vacuum level selection switch, and a stimulation mode switch; and (c) a controller coupled to the cumulative vacuum pump including the release valve and at least the expression mode cycle time switch, the peak vacuum level selection switch, and the stimulation mode selection switch. The electronically controlled breast pump is adapted to provide at least three discreet expression mode vacuum cycle time settings, at least five discreet peak vacuum level settings, and at least one discreet stimulation mode vacuum cycle time setting.

In one preferred embodiment, an electronically controlled cumulative vacuum breast pump includes a pump head communicating with a suction valve and an exhaust valve as well as a groove traversing top dead center of the pump head. The groove traversing top dead center of the pump head is operative to ameliorate vacuum lock of the diaphragm upon motion thereof.

In another preferred embodiment, a four-layer assembly for the electronically controlled breast pump includes: (a) a suction/exhaust manifold plate having a suction line communicating with a release line and an exhaust port isolated from the suction line and release line; (b) a valve membrane plate juxtaposed with the suction/exhaust manifold plate having a suction valve flap communicating with the suction line of the manifold plate and an exhaust flap communicating with the exhaust port of the manifold plate and a release aperture as well as a safety aperture communicating with the release line of the manifold plate; (c) a pump head plate juxtaposed with the valve membrane plate which defines a vacuum chamber as well as the suction aperture communicating with the suction line of the manifold plate, an exhaust aperture communicating with the exhaust port on the manifold plate, a release aperture communicating with the release line of the manifold plate, and a safety aperture communicating with the release line of the manifold plate; and (d) a diaphragm membrane juxtaposed with the pump head plate having a release valve portion, a diaphragm portion, and a safety valve portion.

In still yet another aspect of the present invention, there is provided an adjustable safety valve communicating with a vacuum line of a cumulative vacuum breast pump comprising an elastomeric membrane with a venting aperture pre-tensioned against the closure member such that the closure member seals the aperture up to a predetermined vacuum level and wherein the tension between the membrane and the closure member is adjustable by virtue of positioning the closure member. Adjustment of the closure member thus adjusts tension between the membrane and the closure member.

BRIEF DESCRIPTION OF THE DRAWINGS

The invention is described in detail below with reference to the drawings wherein like numerals designate similar parts. In the drawings.

DETAILED DESCRIPTION OF THE INVENTION

The invention is described in detail below for purposes of exemplification and illustration only. Modifications to particular embodiments within the spirit and scope of the present invention, set forth in the appended claims, will be readily apparent to those of skill in the art.

Figure 1:
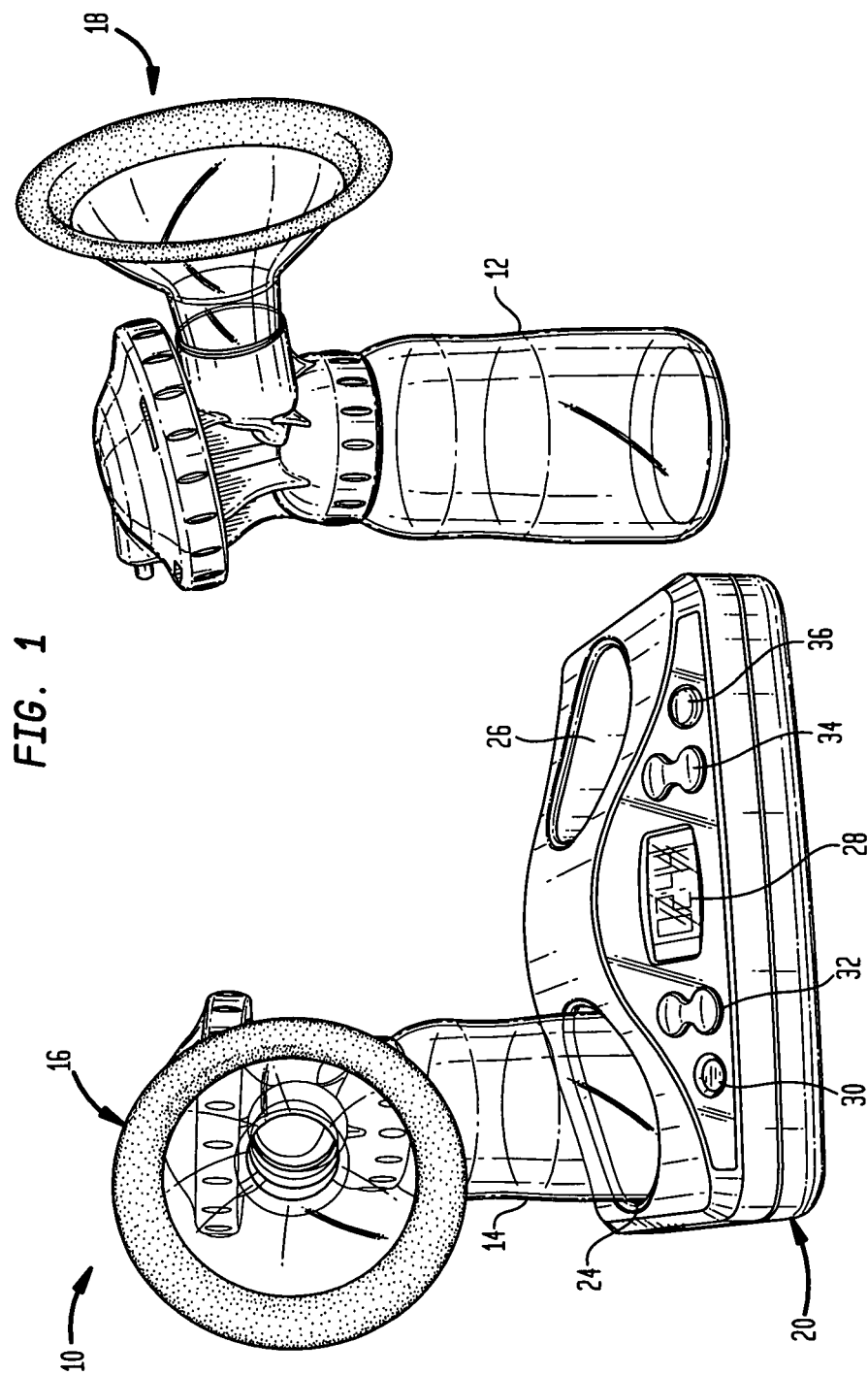
FIG. 1 is a view in perspective of a vacuum pump console and a pair of collection bottles constructed in connection with the present invention.

Referring to FIG. 1, there is illustrated a double electric breast pump system 10 which includes a first collection bottle 12 and a second collection bottle 14. Each of the bottles includes a breast shield 16, 18 for receiving a breast. A console 20 houses an electric cumulative vacuum pump 22 as well as a microprocessor (not shown) and a plurality of switches described hereinafter. Console 20 also has a first cavity 24 and a second cavity 26 for receiving bottles 12 and 14.

Also provided on console 20 is an LCD display 28, an on/off switch 30, and expression mode cycle time selection switch 32, a peak vacuum level selection switch 34, and a stimulation mode switch 36.

Figure 2:
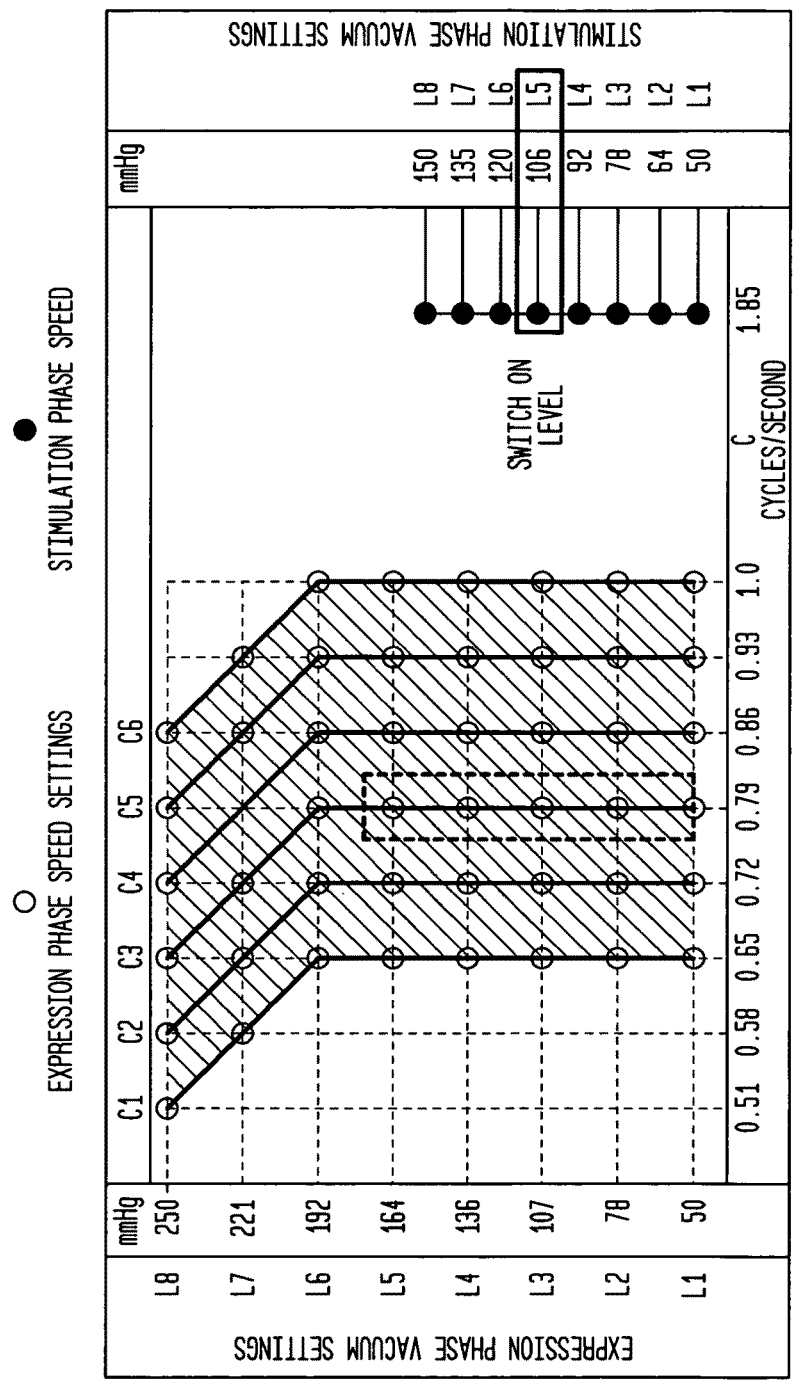
FIG. 2 is a diagram illustrating expression phase cycle time settings and pressures as well as stimulation phase vacuum settings.

The microprocessor controls the cumulative vacuum pump to provide a plurality of operating modes as is seen in FIG. 2.

Figure 3:
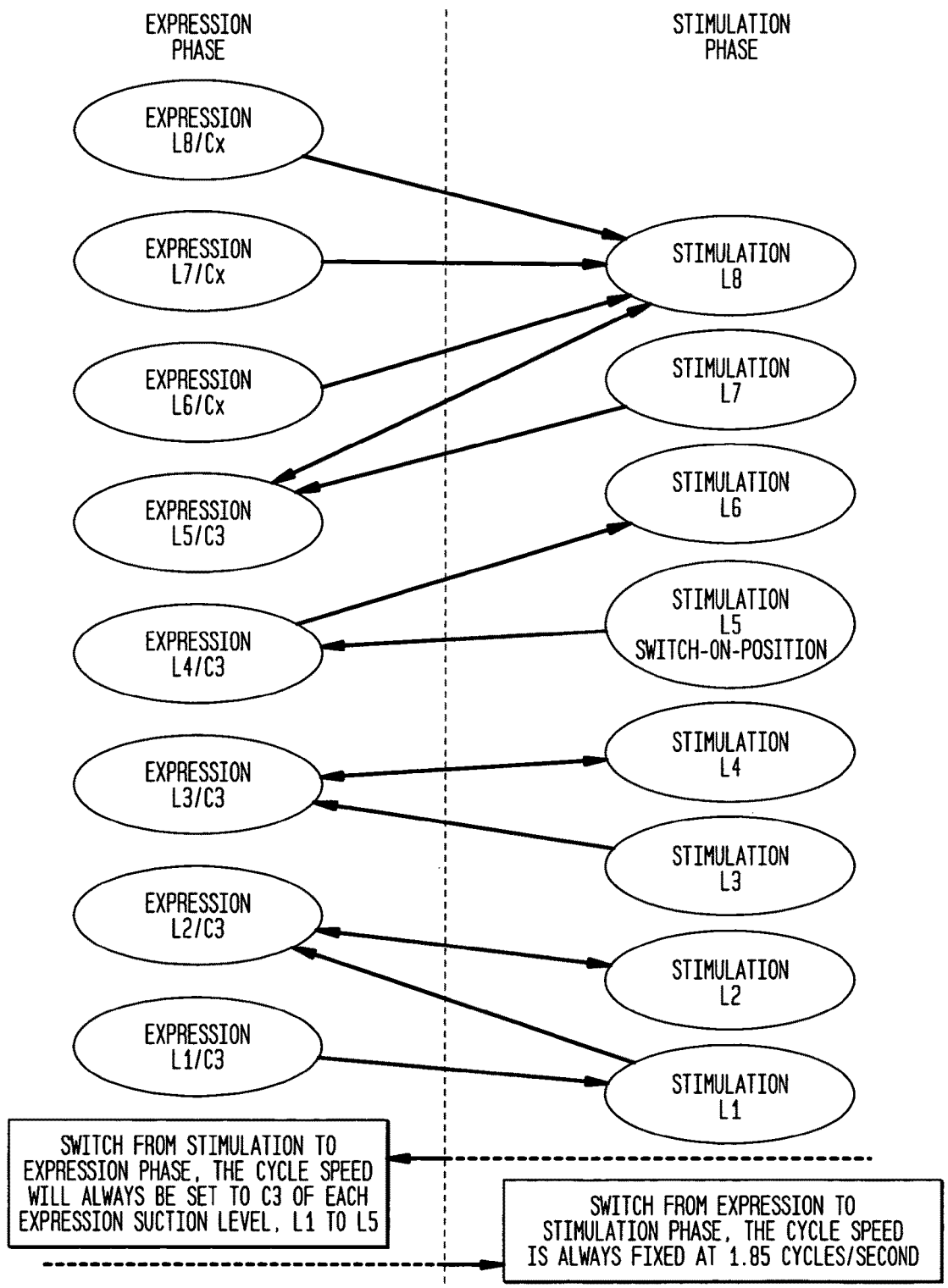
FIG. 3 is a schematic diagram illustrating transitions from an expression phase operation to and from a stimulation phase operation of the present invention.

It is seen in FIG. 2 that the breast pump system shown in FIG. 1 is operated in an expression mode or a stimulation mode. The peak vacuum pressure in the expression mode is selected to be between about 50 and 250 mm of mercury, while the cycle time is selected to be between about 0.5 and 1 cycles per second. In a stimulation mode or "let-down" mode, as is well known in the art, the apparatus 10 is operated at a cycle speed of about 1.85 cycles per second and at a vacuum pressure between about 50 and 150 mm of mercury. The apparatus is switched between the expression mode and the stimulation mode either automatically upon start up or by pressing button 36 to provide higher frequency stimulation. The various control schemes are shown in FIG. 3. In FIG. 3 it is seen that in switching from expression to stimulation mode, the cycle speed is always fixed at 1.85 cycles per second; whereas in switching from stimulation to expression mode, the cycle speed will always be set to a third level of each expression suction level L1 to L5 as shown in the diagram. Typical operating parameters for the system are provided below in Tables 1 and 2.

TABLE 1

EXPRESSION PHASE VACUUM LEVEL & CYCLE SPEED SETTINGS TABLE

| Vacuum Level | Cycle Speed Settings | | | | | | | | | | | |
|---|---|---|---|---|---|---|---|---|---|---|---|---|
| | C1 | | C2 | | C3 | | C4 | | C5 | | C6 | |
| Settings (mmHg) | Cycle/sec | Cycle/min | Cycle/sec | Cycle/min | Cycle/sec | Cycle/min | Cycle/sec | Cycle/min | Cycle/sec | Cycle/min | Cycle/sec | Cycle/min |
| L1  50 | 0.65 | 39 | 0.72 | 43 | 0.79 | 47 | 0.86 | 52 | 0.93 | 56 | 1.0 | 60 |
| L2  78 | 0.65 | 39 | 0.72 | 43 | 0.79 | 47 | 0.86 | 52 | 0.93 | 56 | 1.0 | 60 |
| L3 107 | 0.65 | 39 | 0.72 | 43 | 0.79 | 47 | 0.86 | 52 | 0.93 | 56 | 1.0 | 60 |
| L4 136 | 0.65 | 39 | 0.72 | 43 | 0.79 | 47 | 0.86 | 52 | 0.93 | 56 | 1.0 | 60 |
| L5 164 | 0.65 | 39 | 0.72 | 43 | 0.79 | 47 | 0.86 | 52 | 0.93 | 56 | 1.0 | 60 |
| L6 192 | 0.65 | 39 | 0.72 | 43 | 0.79 | 47 | 0.86 | 52 | 0.93 | 56 | 1.0 | 60 |
| L7 221 | 0.58 | 35 | 0.65 | 39 | 0.72 | 43 | 0.79 | 47 | 0.86 | 52 | 0.93 | 56 |
| L8 250 | 0.51 | 31 | 0.58 | 35 | 0.65 | 39 | 0.72 | 43 | 0.79 | 47 | 0.86 | 52 |

TABLE 2

STIMULATION PHASE VACUUM LEVEL SETTINGS

| Vacuum Level Settings (mmHg) | Cycle speed setting C | |
|---|---|---|
| | Cycle/sec | Cycle/min |
| L1 | 50 | 1.85 | 111 |
| L2 | 64 | 1.85 | 111 |
| L3 | 78 | 1.85 | 111 |
| L4 | 92 | 1.85 | 111 |
| L5 | 106 | 1.85 | 111 |
| L6 | 120 | 1.85 | 111 |
| L7 | 135 | 1.85 | 111 |
| L8 | 150 | 1.85 | 111 |

Figure 4:
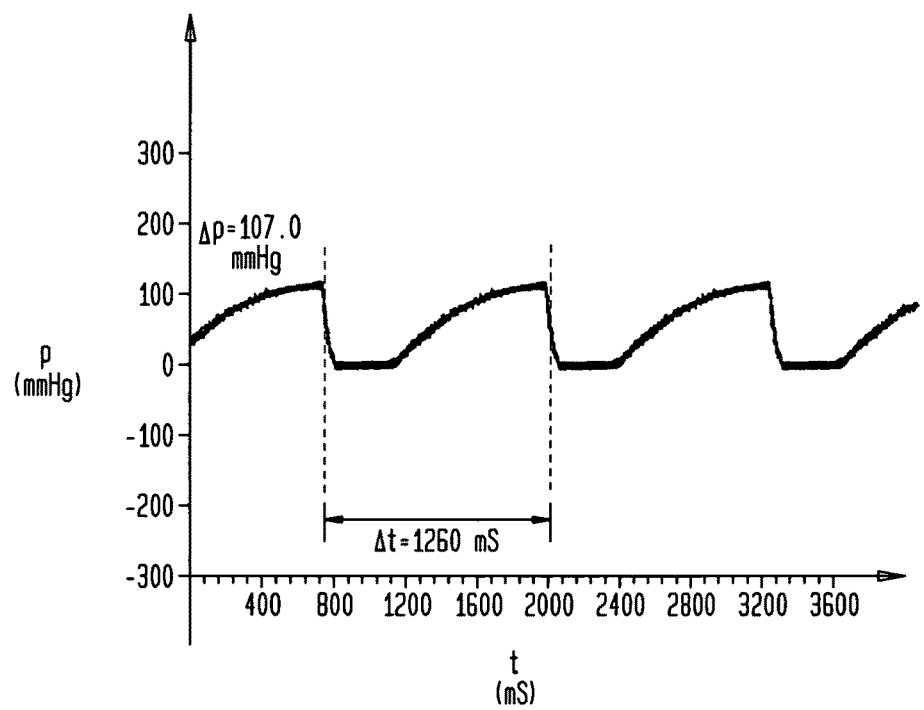
FIG. 4 is a plot of pressure vs. time illustrating a typical expression phase pressure/cycle time profile of the vacuum pump system of the present invention.

A typical suction curve for expression mode is shown in FIG. 4. In FIG. 4 the breast pump system 10 generates a peak vacuum of about 100 mm of mercury at a cycle time of about 0.8 seconds per cycle. As can be seen, a typical curve has a cyclical suction profile which mimics the suction of an infant on a breast. Of course, the simple curve shown in FIG. 4 is similarly achieved at the other levels shown in Table 1.

Figure 5:
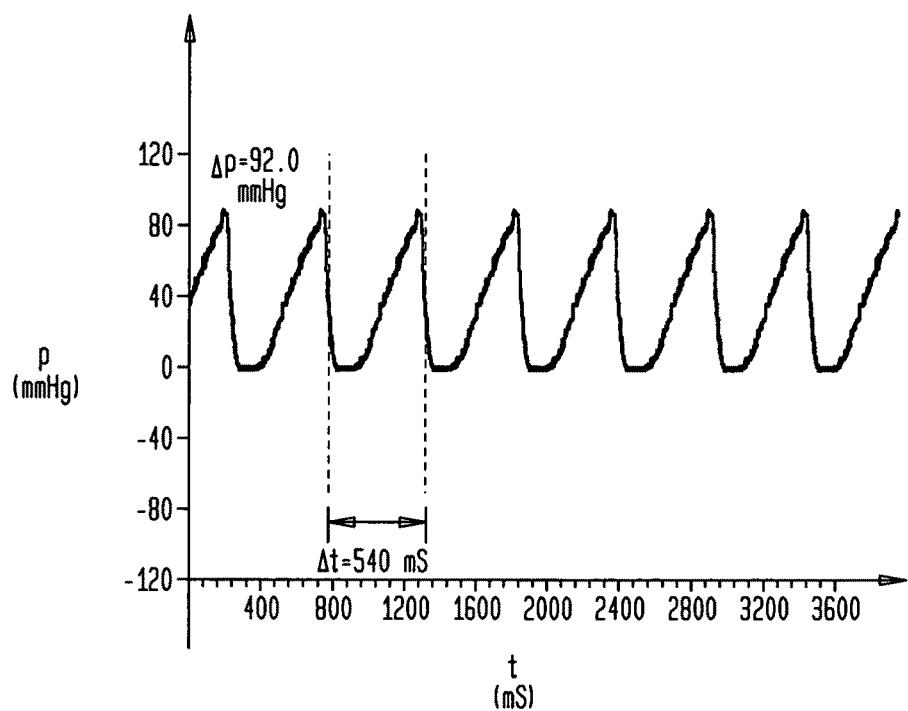
FIG. 5 is a plot of vacuum pressure vs. time for a typical let-down phase (stimulation phase) operation of the vacuum pump system of the present invention.
Figure 6:
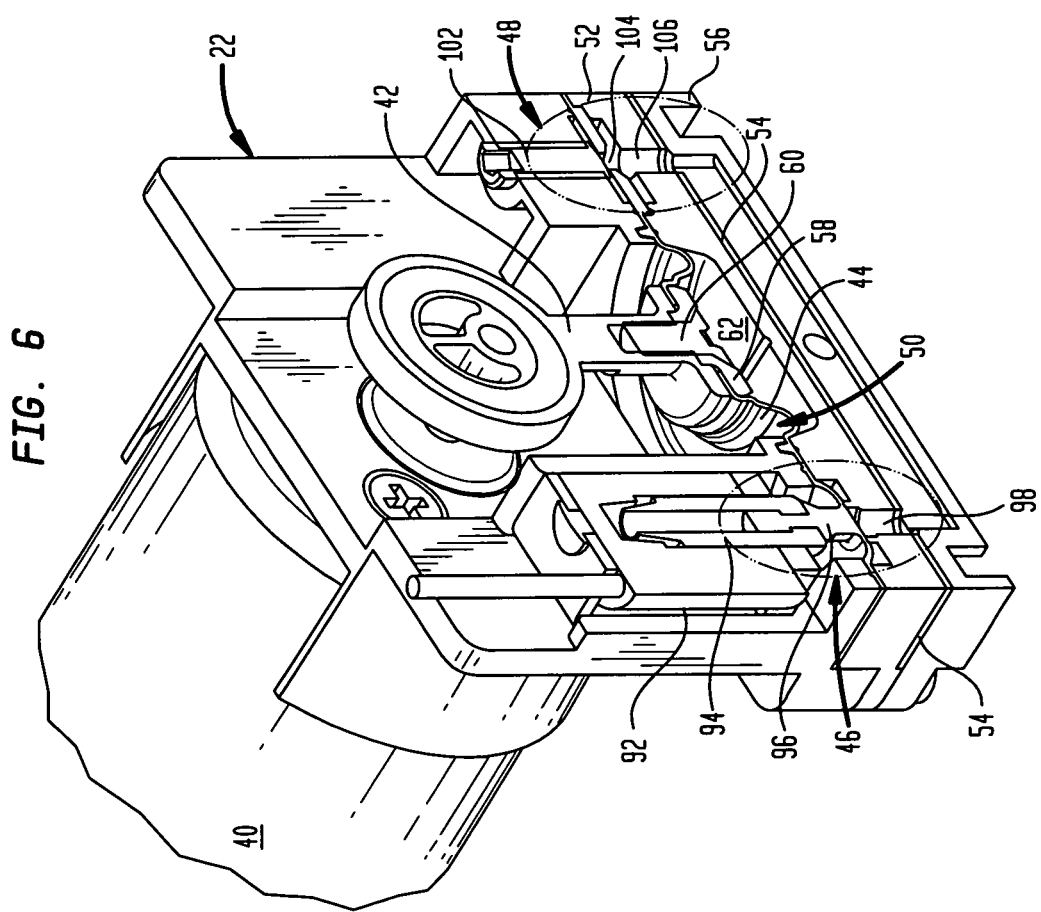
FIG. 6 is a schematic view, in section, of a vacuum pump unit constructed in accordance with the present invention.
Figure 7:
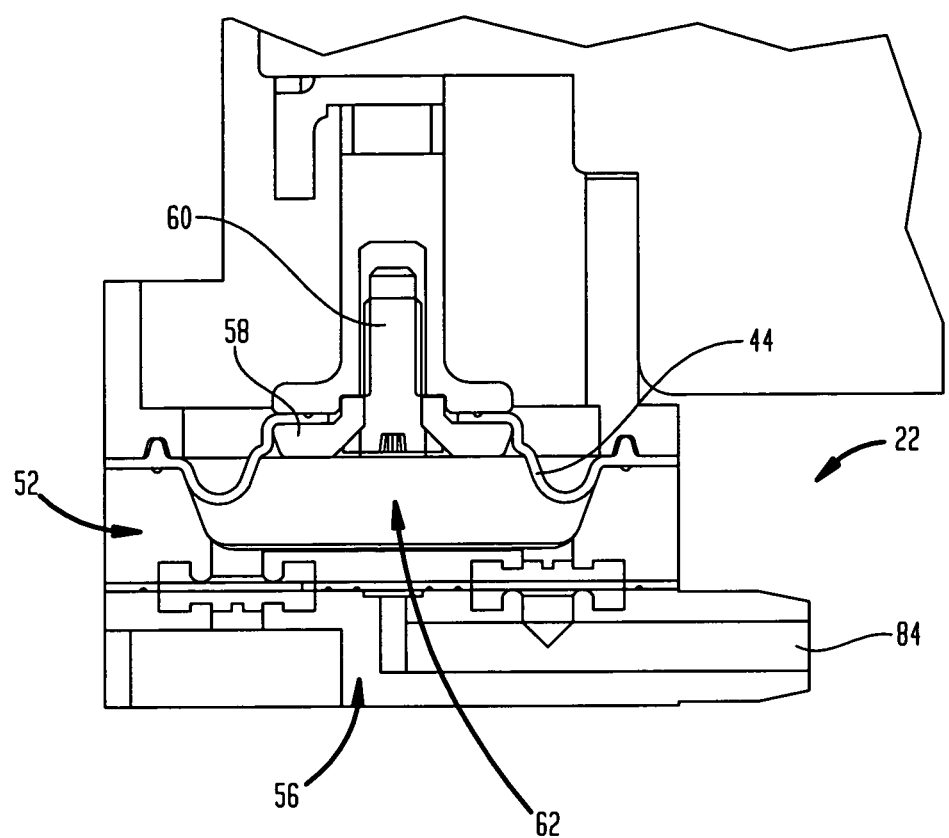
FIG. 7 is another schematic view, in section, of the vacuum pump unit of FIG. 6.
Figure 8:
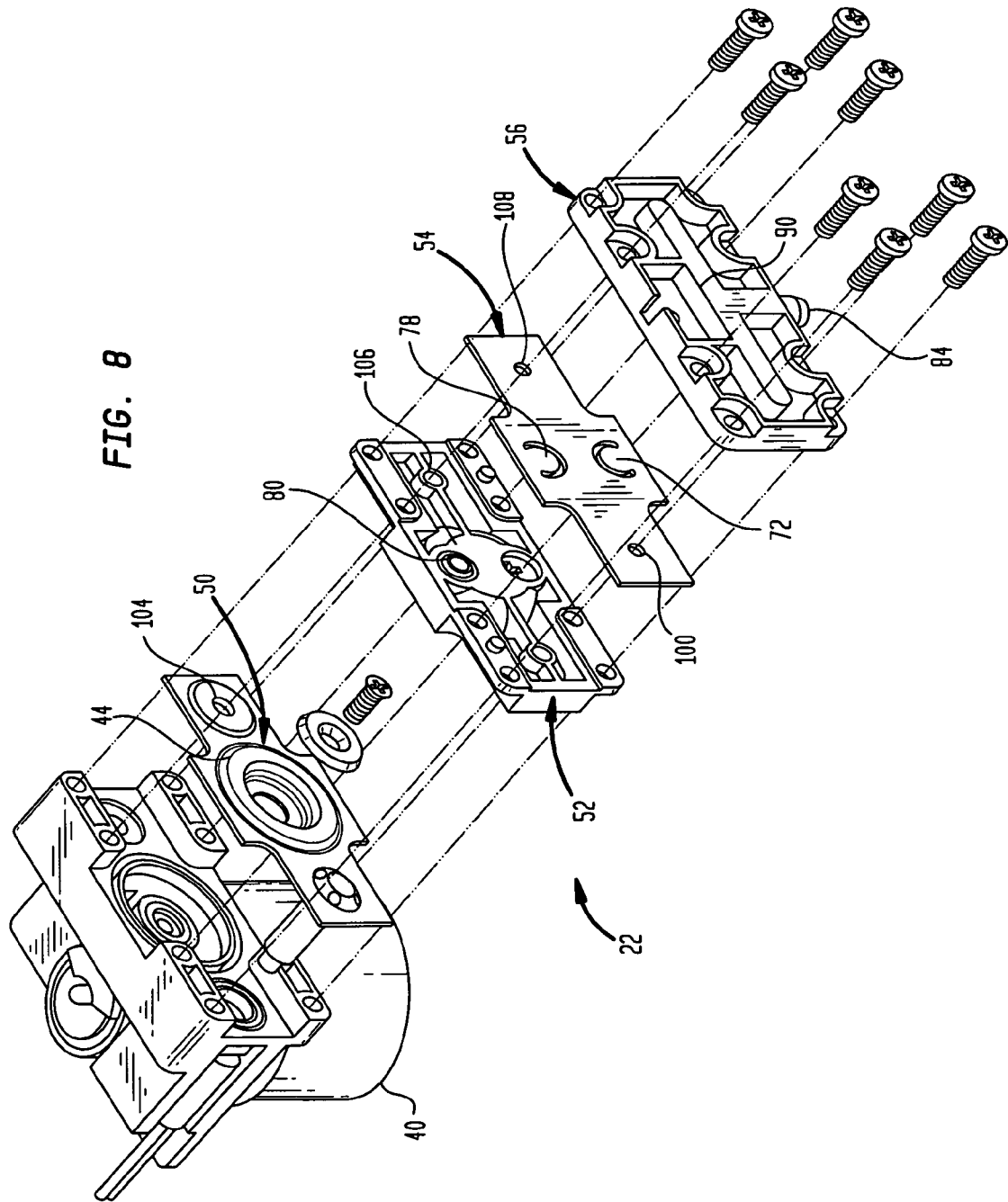
FIG. 8 is an exploded view of the vacuum pump unit of FIGS. 6 and 7.
Figure 9:
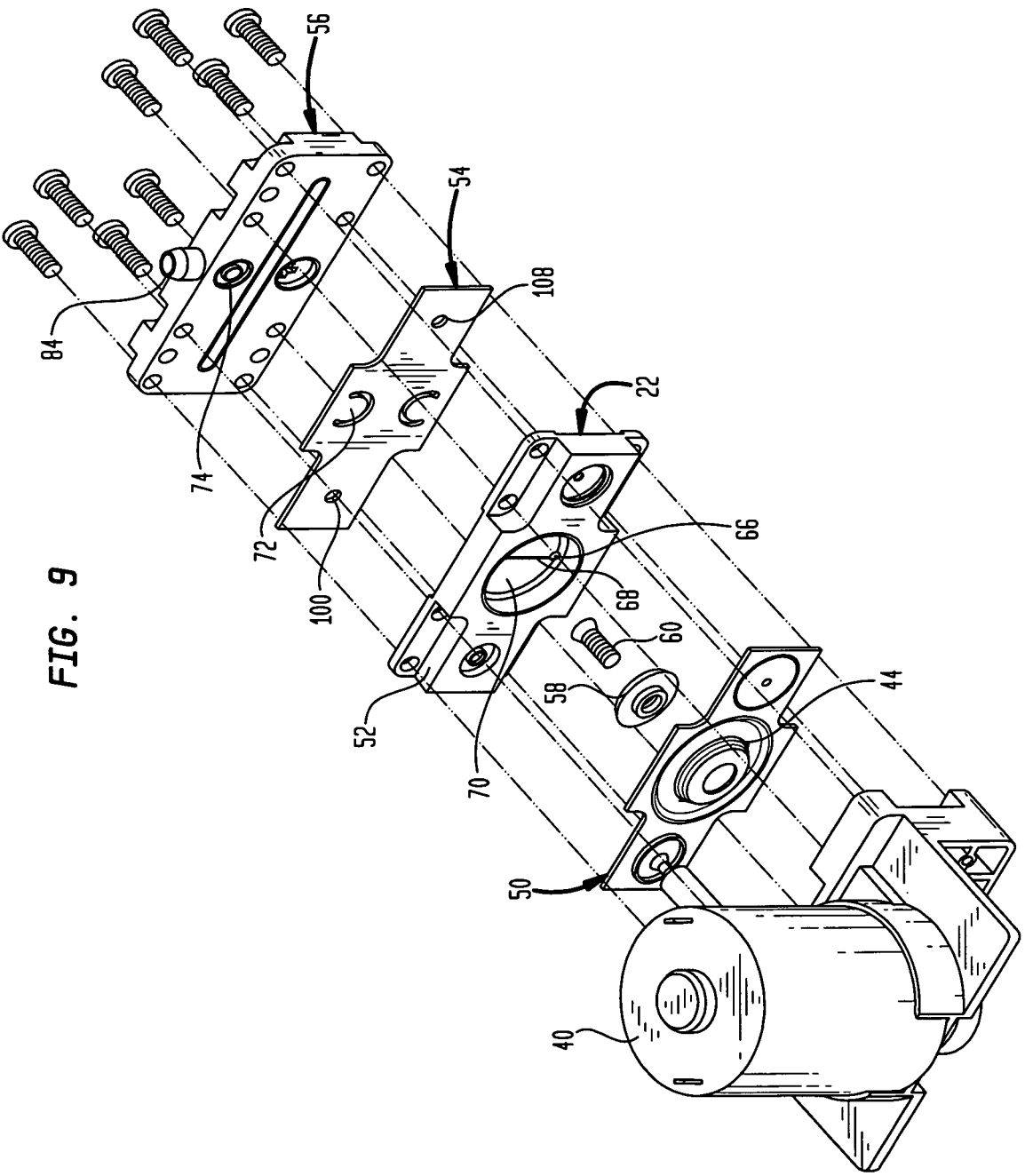
FIG. 9 is another exploded view of the vacuum pump unit of FIGS. 6, 7, and 8.
Figure 10:
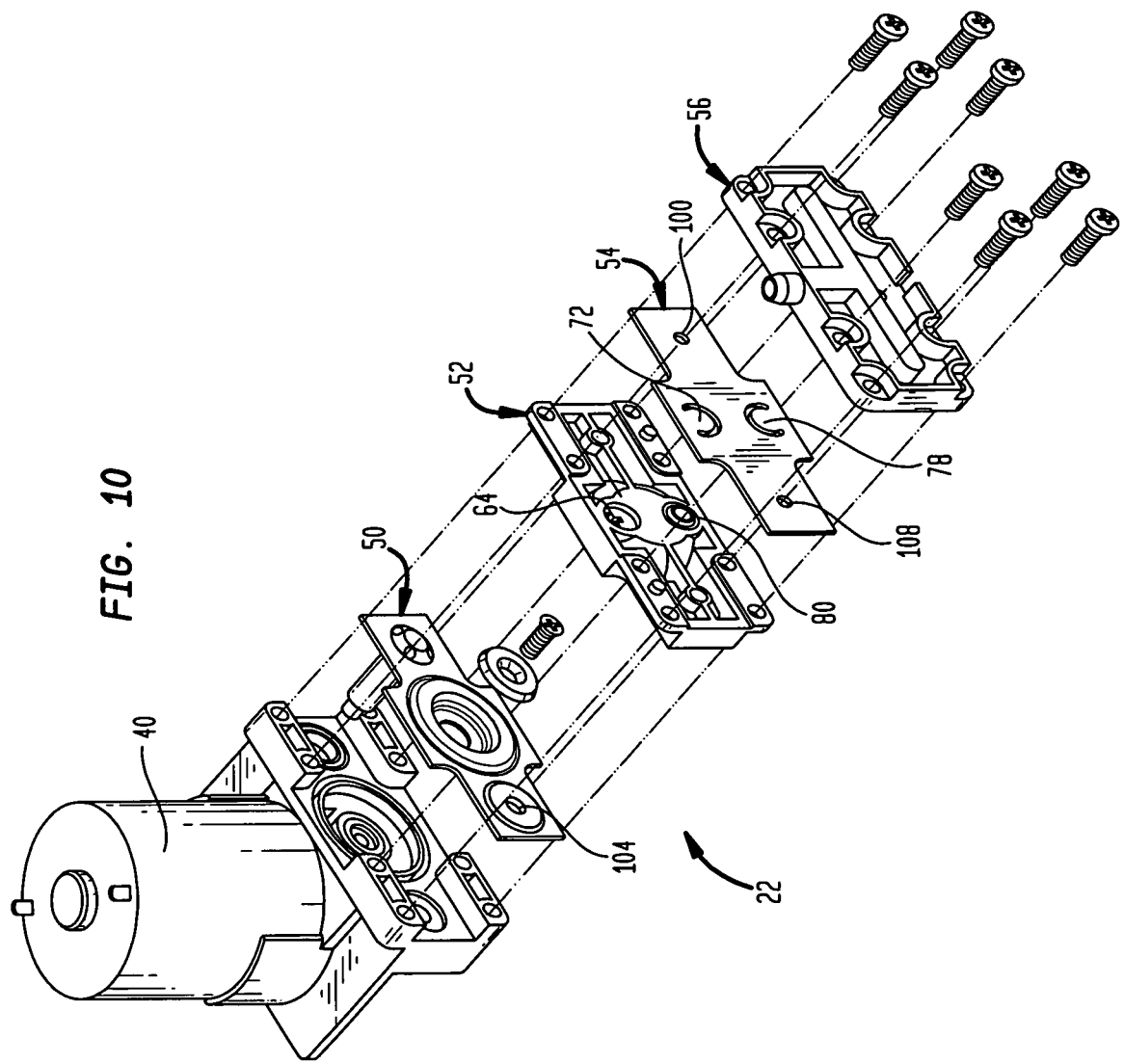
FIG. 10 is yet another exploded view of the vacuum pump unit of FIGS. 6-9.

FIG. 5 is a typical cyclical suction curve for stimulation mode operation of the breast pump apparatus 10. In FIG. 5 it is seen that the vacuum is set at a peak vacuum of about 92 mm of mercury and a cycle time at about 1.85 cycles per second. Other pressure settings are likewise selected by operation of switch 34 on system 10, as is shown above in Table 1.

The various features of system 10 are better appreciated by reference to FIGS. 6-14 which illustrate a cumulative vacuum pump 22 with its various features.

Cumulative vacuum pump 22 includes a motor 40, a connecting rod 42, a pump diaphragm 44, as well as a release unit 46. Also provided is as a safety unit 48. Pump diaphragm 44 is part of a diaphragm membrane 50 which is juxtaposed with a pump head plate 52. Also provided are a membrane plate 54 and a suction/exhaust manifold plate 56. Motor 40 is eccentrically coupled to connecting rod 42, which in turn is secured to diaphragm 44 with a mounting washer 58 as well as a screw 60. As the motor turns, the connecting rod drives the diaphragm toward the pump head plate 52 in order to actuate the pump. The connecting rod may also draw the diaphragm away from the pump head or simply allow the diaphragm to return to the position shown in FIG. 6 by virtue of elastic recovery. The diaphragm is suitably made from any suitable elastomeric material such as acrylic elastomers; butyl rubber; chlorosulfonated polyethylene; ethylene-propylene rubber; fluorinated elastomers; neoprene; nitrile rubber; polybutadiene; polyethers; polyisoprene; polypentenamers; styrene-butadiene rubber; and thermplastic elastomers. See, *Kirk-Othmer Encyclopedia of Chemical Technology*, $3^{rd}$ Ed., Vol. 8 pp. 446-640, the disclosure of which is incorporated herein by reference. Other rubbers from which the pump diaphragm may be made include silicone rubber or natural rubber based materials. Suitable silicone rubber materials are described in *Kirk-Othmer Encyclopedia of Chemical Technology*, $3^{rd}$ Ed, Vol. 20, pp. 943-53, the disclosure of which is incorporated herein by reference The process generates vacuum due to the configuration and valving of the system. To this end, pump head plate 52 defines a vacuum chamber 62 which is provided with a suction valve aperture 64 as well as an exhaust valve aperture 66. Between apertures 64 and 66 there is provided a groove 68 across top dead center of pump head 70. Groove 68 provides dead space at top dead center of pump head 70 in order to ameliorate "vacuum lock" of the diaphragm as it reciprocates and generates vacuum.

Suction valve aperture 64 is adjacent a suction valve flap 72 on membrane plate 54. A suction valve seat 74 is provided on suction/exhaust plate 56 such that the suction valve communicates with a suction line 84.

Exhaust valve aperture 66 is juxtaposed with an exhaust valve flap 78 on membrane plate 54. The exhaust valve flap has a seat 80 on pump head plate 52. When diaphragm 44 moves toward and away from the pump head, the valves operate as follows. When diaphragm 44 moves toward pump head 70, flap 78 will unseat from valve seat 80 and exhaust the exhaust air from chamber 62 to exhaust port 82.

When diaphragm 44 moves away from pump head 70, suction valve flap 72 unseats from valve seat 74 of suction/exhaust manifold plate 56, thus opening the aperture. At the same time, exhaust flap 78 will seat on seat 80, thus sealing the vacuum chamber such that vacuum is applied to a vacuum line 84 of the unit. Thus it is seen that the vacuum chamber communicates with the vacuum line through suction valve aperture 64 and suction valve flap 72 upon motion of the diaphragm away from the pump head; and the vacuum chamber communicates with exhaust port 82 upon motion of the diaphragm toward the cylinder head through exhaust valve aperture 66 and exhaust valve flap 78, thus generating a vacuum producing cycle. Inasmuch as pump 22 is a cumulative vacuum pump, the various components are typically selected and operated such that a maximum vacuum occurs at roughly 80 revolutions (or strokes) in one preferred construction.

The inventive system may thus be operated with a relatively low power motor, i.e., a 5 or 10 watt motor. The power required to drive our pump at maximum load is 5 W, not 10 W; however we are using a larger motor for our application in order to allow for possible future modifications in the system software and hardware. The motor may be battery driven and yet still generate the relatively high levels of vacuum seen in FIGS. 4 and 5 as well as Tables 1 and 2 above. In this respect, the motor may be driven by wall current or by AA alkaline batteries, for example.

It is important in a cumulative vacuum pump to carefully control the vacuum with a release valve in order to optimize performance, i.e., it is desirable that the exhaust stroke of the diaphragm coincides with a release of a cumulative vacuum to complete a vacuum cycle applied to line 84. That is to say, the vacuum seen by line 84 is that plotted in FIGS. 4 and 5, for example.

Thus, the vacuum applied to line 84 is largely controlled by release unit 46 which, in turn, is controlled by the microprocessor which is connected to the switches on control console 20.

Release unit 46 includes a solenoid 92 with an actuator 94 which is attached to a release portion 96 of diaphragm membrane 50. Pump head plate 52 includes a release channel 98 which communicates with a release aperture 100 of membrane plate 54 which in turn communicates with release line groove 90 of suction/exhaust manifold plate 56. Thus, release channel 98 communicates with vacuum line 84 to release the vacuum therein upon actuation by the microprocessor control unit in console 20. The number of strokes between venting may be any suitable number, as noted above maximum vacuum of about 250 mm of mercury or so is reached after about 80 vacuum cycles (1 suction cycle). Note that the air flow through release unit 46 may be provided by a plurality of apertures such as apertures 46a, 46b in diaphragm membrane 50.

Although the release unit is extremely reliable, a safety unit is also provided so that excess vacuum will not be applied to line 84. To this end, safety unit 48 includes a set screw 102 which communicates with an aperture 104 in diaphragm membrane 50. Aperture 104 communicates with another aperture 106 in pump head plate 52. In operation set screw 102 is advanced onto membrane plate 54 such that there is a tension between the screw and the region of the membrane plate at the safety unit. That is to say, screw 102 bears upon membrane 50 at an area close to aperture 104 in membrane 50. Aperture 104 communicates with aperture 106 which, in turn, communicates with release line groove 90 through a third aperture 108 in membrane plate 54. Thus, when a predetermined amount of vacuum builds up in line 84, the vacuum will draw membrane plate 50 away from set screw 102 and allow air to enter the system, thus breaking the vacuum. A predetermined safety level can be set by adjusting screw 102. That is to say, additional tension will supply a higher release threshold for the safety unit. Thus, if the release unit does not properly vent the system to provide the desired peak pressure, the safety unit will allow air to enter the system at a predetermined vacuum level and insure that a preset peak vacuum level is not exceeded.

Figure 11:
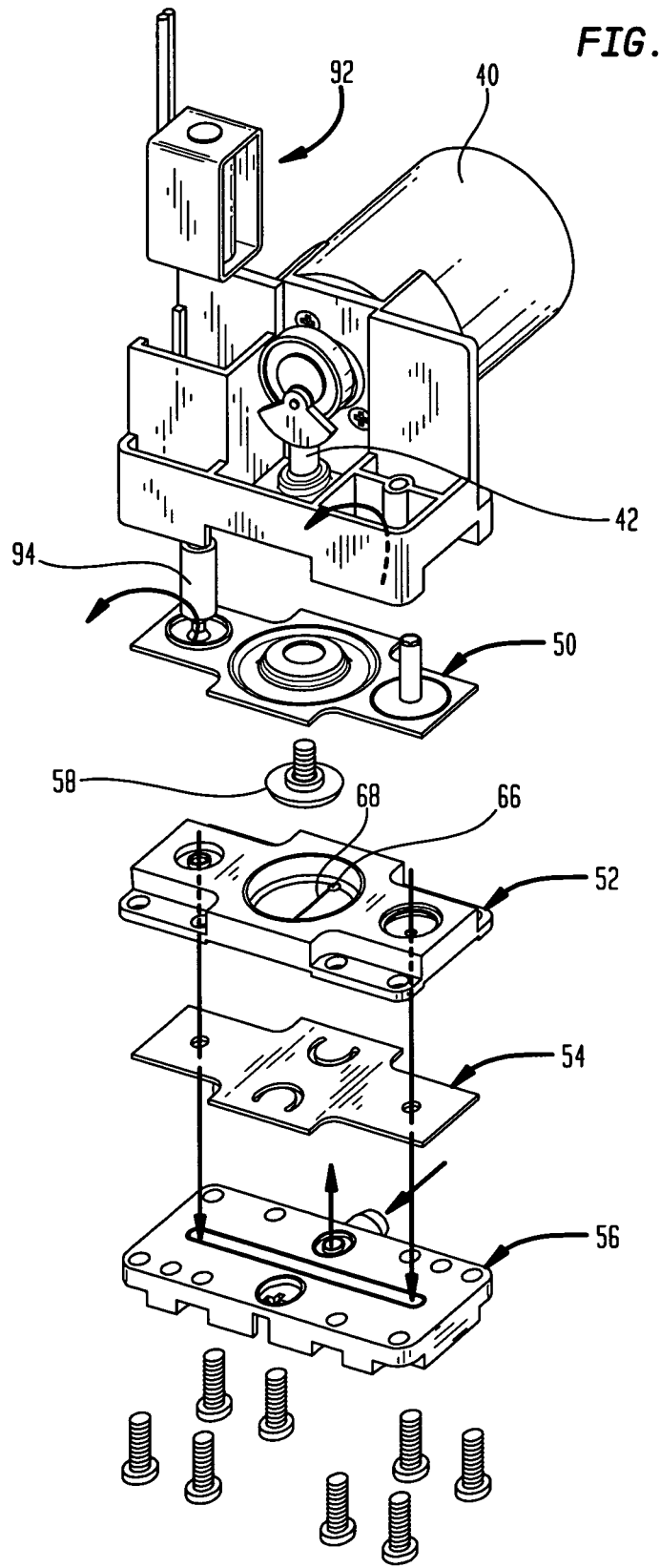
FIG. 11 is still yet another exploded view of the vacuum pump unit of FIGS. 6-10, schematically illustrating air flow.
Figure 12:
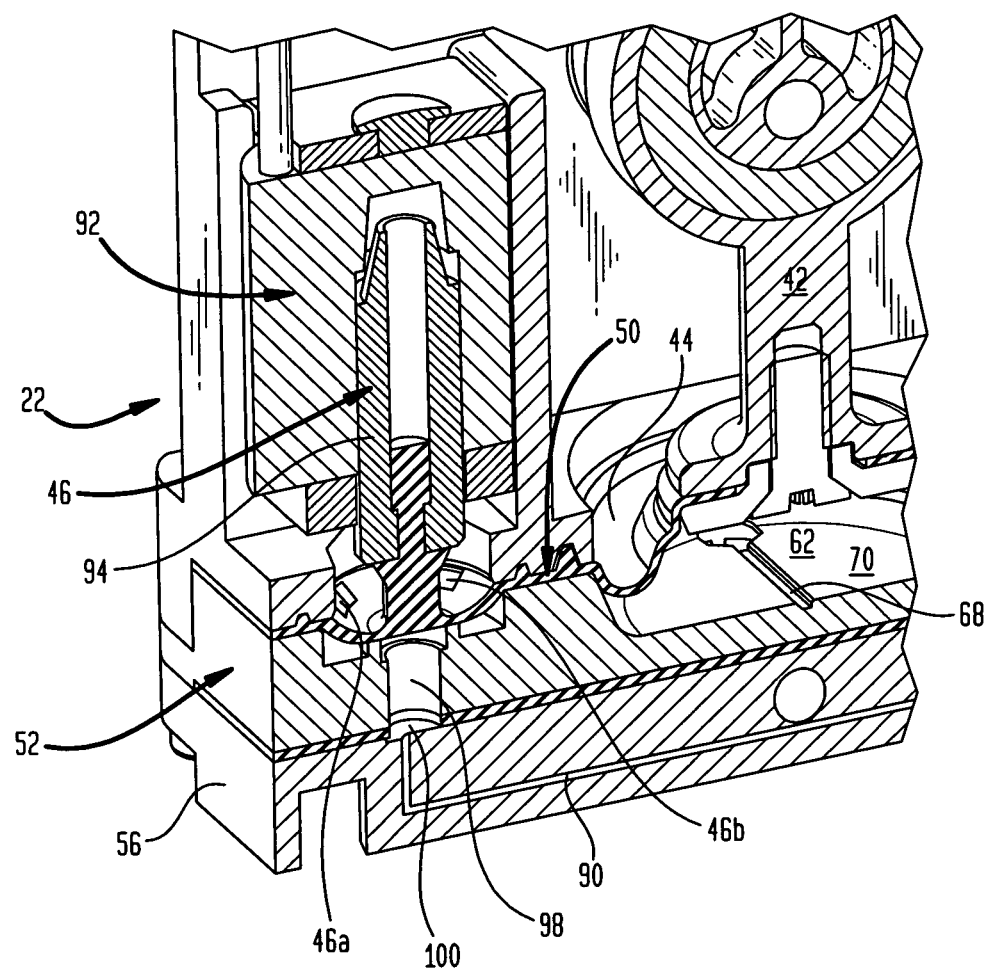
FIG. 12 is a partial schematic view, in section, illustrating the release mechanism of the vacuum pump unit of FIGS. 6-11.
Figure 13:
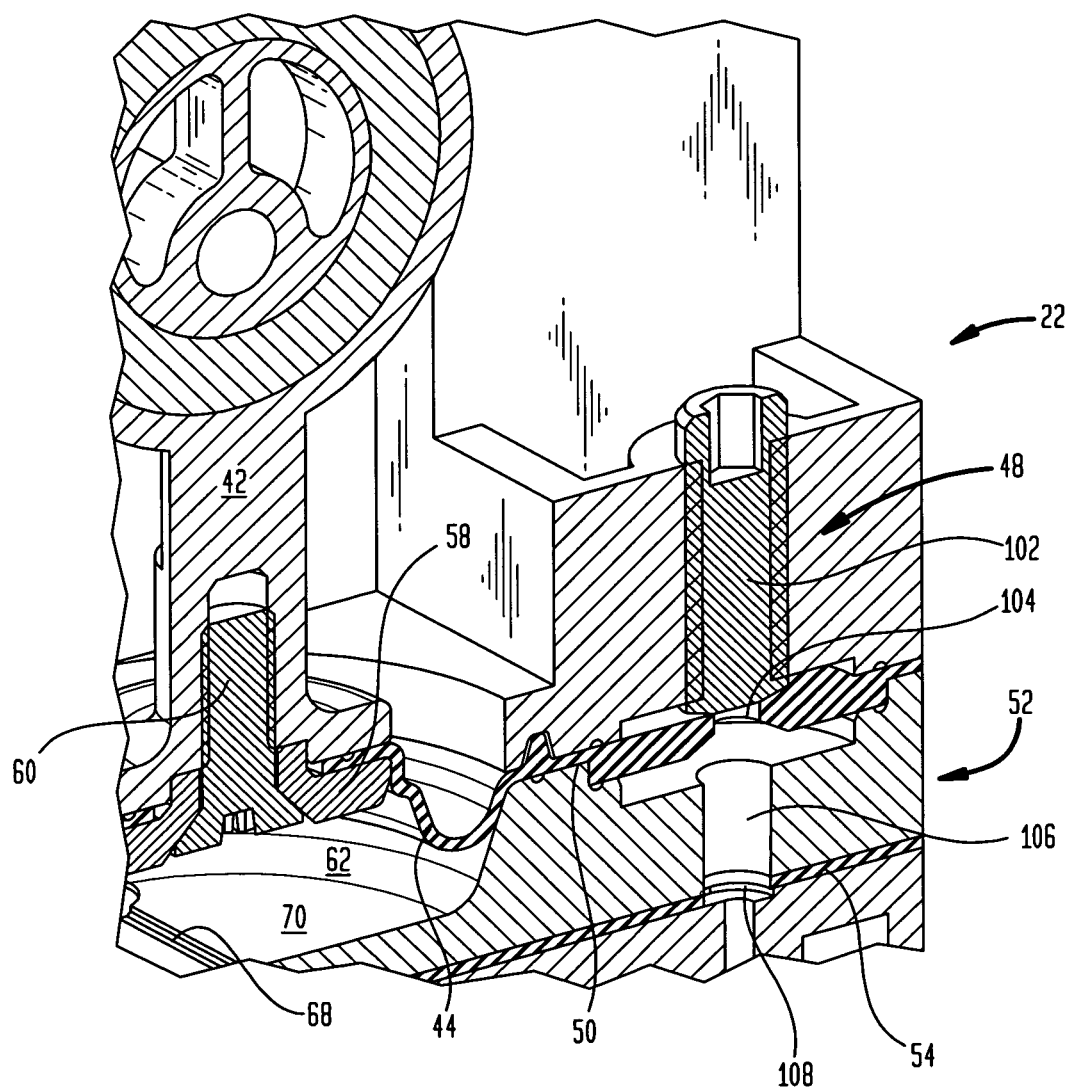
FIG. 13 is a schematic partial view, in section, illustrating the safety vent release valve of the vacuum pump unit of FIGS. 6-11.
Figure 14A:
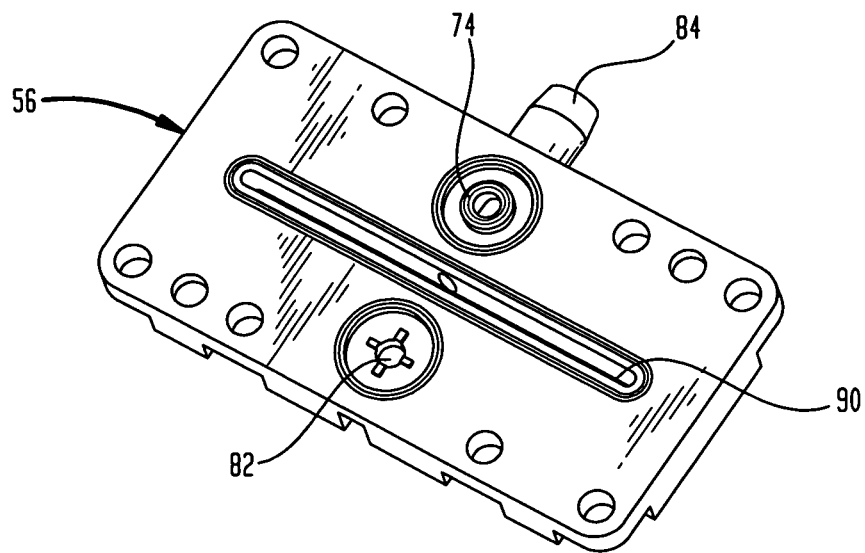
FIGS. 14A and 14B are a detail of the vacuum pump unit of FIGS. 6-11 illustrating the suction/exhaust manifold of the vacuum pump unit.
Figure 14B:
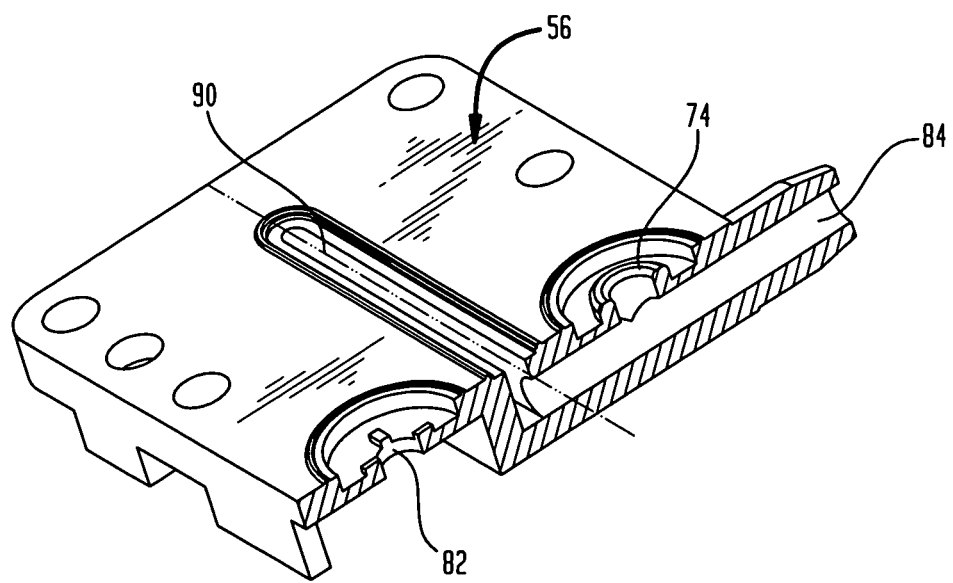

The various air flow paths are indicated schematically on FIG. 11 by a plurality of arrows.

Thus, summarizing the above, the cumulative vacuum pump of the present invention is operated in connection with two flap valves. The vacuum phase starts when the vacuum diaphragm is advanced all the way to the pump head. The exhaust flap closes the exhaust line and the suction flap opens the vacuum line, and vacuum is realized due to the connection of the vacuum line to the vacuum bottle and the sealing of the system against the breast of a user. Vacuum is generated over a number of cycles before it is released by the release unit. In this way, the desired vacuum level and cycle times are achieved. The release system is controlled by way of the console switches and microprocessor as described above. The inventive pump is the only mobile cumulative vacuum breast pump available which allows a mother to vary the cycle speed within a limited comfort range, at a given set suction vacuum level setting. This actually allows the user to adjust her own comfort level of extracting milk from her breast. As in nature, if examined randomly, each baby has a different suction repetition rate at a given suction strength level. Therefore; since we are providing a pump with natural suction characteristics, it is important that we give the mother a capacity to adjust the suction repetition rate within the set suction power level and this pump does just that. The mother can conveniently fine-tune tune her suction pattern to match the natural suction characteristics of her baby, which is unique to herself and to her baby. Existing cumulative vacuum pumps generally only allow the mother to select the suction power and the control electronics allocates a predetermined suction repetition rate for the selected suction power level, where the mother cannot change or adjust. She is limited to a predetermined cycle rate programmed into the pump memory. The inventive system introduces the ability to adjust the cycle rate at any given suction power level, from L1 to L8 as noted above.

The air outlet phase starts when the membrane is withdrawn to the top of the stroke, i.e. away from the pump head. The suction flap closes the suction line as the diaphragm moves down and the exhaust flap opens to allow air to escape from the previous pump cycle. Approximately 80 diaphragm movements are required for achieving maximum vacuum level from this product.

The release valve can be opened by a linear solenoid according to adjustments or control from the microprocessor. In this way the vacuum line is open to the atmosphere and controlled set air release phase started. By controlling the release times, the desired suction cycles such as those shown in Table 1 and FIGS. 4 and 5 are completed. The release unit is controlled with a dedicated algorithm in order to save energy and increase the life time of the solenoid by applying variable controlled power to the solenoid windings, depending on the selected suction level settings. The power required in order to release the diaphragm membrane varies according to the opposing vacuum force, which in turn applies a pulling action away from the solenoid plunger, hence the higher the vacuum setting, more pulling force is required to move the diaphragm membrane away from the venting hole and depending on the vacuum level setting, the required pull force, hence the required power to the solenoid varies. Therefore considerable power saving and lifetime extension of the solenoid is provided by applying low power for low level vacuum settings and high power for higher level vacuum settings.

The vacuum level is also limited by placing a safety valve communicating with the suction vacuum line. The safety level is adjusted with a screw. Placement of the screw determines the preload on the safety diaphragm, i.e., in the vicinity of the aperture, and thus provides an adjustable, yet predetermined safety threshhold. When the vacuum level gets above the defined safety level, the force generated by vacuum exceeds the preloaded force. In this situation, the air flow is realized to the suction line and breaks the vacuum. That is to say, the vacuum level decreases because of the air entering the suction line through the safety unit. The channel will close when the balance between pressure force is created and the force created by the preload is achieved. In this way, protection from extreme vacuum levels is always present, even in the event of failure of the release unit.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. An electronically controlled breast pump for generating cyclical suction comprising:
   (a) a vacuum pump unit with a release valve;
   (b) a plurality of switches including at least an expression mode cycle time selection switch, a peak vacuum level selection switch and a stimulation mode switch; and
   (c) a controller coupled to the vacuum pump unit, including the release valve and at least the expression mode cycle time selection switch, the peak vacuum level selection switch and the stimulation mode selection switch,
wherein the electronically controlled breast pump is adapted to provide at least 3 discrete expression mode vacuum cycle time settings, at least 5 discrete peak vacuum level settings and at least 1 discrete stimulation mode vacuum cycle time setting, and wherein a plurality of discrete peak vacuum level settings are selectable in said stimulation mode.

2. An electronically controlled breast pump for generating cyclical suction according to claim 1 comprising
   a cumulative vacuum pump,
wherein the cumulative vacuum pump includes one or more of the following:
   (i) a vacuum pump with a four layer assembly including:
      (A) a suction/exhaust manifold plate having a suction line communicating with a release line and an exhaust port isolated from the suction line and release line;
      (B) a valve membrane plate juxtaposed with a suction valve flap communicating with the suction line of the manifold plate and an exhaust flap communicating with the exhaust port of the manifold plate and a release aperture as well as a safety aperture communicating with the release line of the manifold plate;
      (C) a pump head plate which defines a vacuum chamber as well as a suction aperture communicating with the suction line of the manifold plate, an exhaust aperture communicating with the exhaust port of the manifold plate, a release aperture communicating with the release line of the manifold plate and a safety aperture communicating with the release line of the manifold plate; and
      (D) a diaphragm membrane juxtaposed with the pump head plate having a release valve portion, a diaphragm portion and a safety valve portion;
   (ii) an adjustable safety valve communicating with a vacuum line of a cumulative vacuum breast pump comprising an elastomeric membrane with a venting aperture pre-tensioned against a closure member such that the closure member seals the aperture up to a predetermined vacuum level and wherein the tension between the membrane and the closure member is adjustable by virtue of positioning the closure member, thereby adjusting the tension between the membrane and closure member; or (iii) a pump head communicating with a suction valve and an exhaust valve as well as a groove traversing top dead center of the pump head.

3. The electronically controlled breast pump for generating cyclical suction according to claim 2, wherein the cumulative vacuum pump includes An adjustable safety valve communicating with a vacuum line of a cumulative vacuum breast pump comprising an elastomeric membrane with a venting aperture pre-tensioned against a closure member such that the closure member seals the aperture up to a predetermined vacuum level and wherein the tension between the membrane and the closure member is adjustable by virtue of positioning the closure member, thereby adjusting the tension between the membrane and closure member.

4. The electronically controlled breast pump for generating cyclical suction according to claim 1, wherein the electronically controlled breast pump is adapted to provide at least 6 discrete expression mode vacuum cycle time settings, at least 8 discrete peak vacuum level settings and at least 1 discrete stimulation mode vacuum cycle time setting.

5. The electrically controlled breast pump for generating cyclical suction according to claim 1, wherein the expression mode vacuum cycle time settings range from about 0.4 cycles per second to about 1.25 cycles per second and the stimulation mode cycle time setting ranges from about 1.5 cycles per second to about 2.5 cycles per second.

6. The electrically controlled breast pump for generating cyclical suction according to claim 1, wherein the expression mode vacuum cycle time settings range from about 0.5 cycles per second to about 1 cycle per second and the stimulation mode cycle time setting range is set at 1.85 cycles/second.

7. The electrically controlled breast pump for generating cyclical suction according to claim 1, wherein the electronically controlled breast pump has at least 7 discrete peak vacuum level settings.

8. The electrically controlled breast pump for generating cyclical suction according to claim 1, wherein the electronically controlled breast pump has at least 5 discrete expression mode vacuum cycle time settings.

9. The electronically controlled breast pump for generating cyclical suction according to claim 1, wherein the peak vacuum level settings range from about 40 m Hg to about 300 mm Hg.

10. The electrically controlled breast pump for generating cyclical suction according to claim 1, wherein the stimulation mode vacuum cycle operates at a selectable peak vacuum level of from 40 mm Hg to about 175 mm Hg.

11. The electronically controlled breast pump for generating cyclical suction according to claim 1, wherein at least 3 discrete peak vacuum level settings are selectable in said stimulation mode.

12. The electronically controlled breast pump for generating cyclical suction according to claim 11, wherein at least 4 discrete peak vacuum level settings are selectable in said stimulation mode.

13. The electronically controlled breast pump for generating cyclical suction according to claim 12, wherein at least 5 discrete peak vacuum level settings are selectable in said stimulation mode.

14. The electronically controlled breast pump for generating cyclical suction according to claim 1, wherein the breast pump is switchable from a plurality of discrete peak vacuum level settings and a stimulation mode vacuum cycle time setting to a predetermined expression mode cycle time setting.

15. An electronically controlled breast pump for generating cyclical suction comprising:
(a) a vacuum pump unit with a release valve;
(b) a plurality of switches including at least an expression mode cycle time selection switch, a peak vacuum level selection switch and a stimulation mode switch; and
(c) a controller coupled to the vacuum pump unit, including the release valve and at least the expression mode cycle time selection switch, the peak vacuum level selection switch and the stimulation mode selection switch, whereby the controller is operable to control vacuum in response to the peak vacuum level selection switch and the stimulation mode selection switch by controlling the release valve in order to provide an output in the form of repeating vacuum pulses with a peak vacuum level,
wherein the electronically controlled breast pump is adapted to provide at least 3 discrete expression mode vacuum cycle time settings, at least 5 discrete peak vacuum level settings and at least 1 discrete stimulation mode vacuum cycle time setting.

16. The electronically controlled breast pump for generating cyclical suction according to claim 15, wherein a plurality of discrete peak vacuum level setting are selectable in said stimulation mode.

17. The electronically controlled breast pump for generating cyclical suction according to claim 15, wherein the release valve comprises a vented membrane communicating with a vacuum source.

18. The electronically controlled breast pump for generating cyclical suction according to claim 15, wherein the breast pump is switchable from at least 3 of discrete peak vacuum level settings and a stimulation mode vacuum cycle time setting to a single predetermined expression mode cycle time setting.

19. The electronically controlled breast pump for generating cyclical suction according to claim 18, wherein the breast pump is switchable from at least 5 discrete peak vacuum level settings and a stimulation mode vacuum cycle time setting to a single predetermined expression mode cycle time setting.

* * * * *